US010698062B2

(12) United States Patent
Yang et al.

(10) Patent No.: US 10,698,062 B2
(45) Date of Patent: Jun. 30, 2020

(54) DIFFUSION MRI METHOD FOR GENERATING A SYNTHETIC DIFFUSION IMAGE AT A HIGH B-VALUE

(71) Applicant: KONINKLIJKE PHILIPS N.V., Eindhoven (NL)

(72) Inventors: Ming Yang, Suzhou (CN); Feng Huang, Suzhou (CN); Yu Li Huang, Suzhou (CN)

(73) Assignee: Koninklijke Philips N.V., Eindhoven (NL)

( * ) Notice: Subject to any disclaimer, the term of this patent is extended or adjusted under 35 U.S.C. 154(b) by 74 days.

(21) Appl. No.: 15/781,197

(22) PCT Filed: Dec. 1, 2016

(86) PCT No.: PCT/EP2016/079359
§ 371 (c)(1),
(2) Date: Jun. 4, 2018

(87) PCT Pub. No.: WO2017/097656
PCT Pub. Date: Jun. 15, 2017

(65) Prior Publication Data
US 2018/0356486 A1    Dec. 13, 2018

(30) Foreign Application Priority Data
Apr. 26, 2016 (EP) .................................... 16166983

(51) Int. Cl.
*G01R 33/563* (2006.01)
*A61B 5/055* (2006.01)
(Continued)

(52) U.S. Cl.
CPC ...... *G01R 33/56341* (2013.01); *A61B 5/0037* (2013.01); *A61B 5/055* (2013.01);
(Continued)

(58) Field of Classification Search
CPC ............ G01R 33/563; G01R 33/56341; G01R 33/56; G01R 33/5608; G01R 33/565;
(Continued)

(56) References Cited

U.S. PATENT DOCUMENTS 7,902,825 B2 * 3/2011 Bammer .......... G01R 33/56509
324/307
2010/0081918 A1    4/2010 Sugiura et al.
(Continued)

FOREIGN PATENT DOCUMENTS

WO    2010116124 A1    10/2010

OTHER PUBLICATIONS

Kawahara et al "Additional Benefit of Computed Diffusion Weighted Imaging for Detection of Hepatic Metastases at 1.5T" Clinical Imaging, 40 (2016) p. 481-485.
(Continued)

*Primary Examiner* — Son T Le

(57) ABSTRACT

Embodiments of the present invention provide a method for generating a synthetic diffusion image. The method comprises the steps of acquiring multiple sets of initial diffusion scan data by means of diffusion weighted magnetic resonance scans at multiple initial b-values, deriving an initial diffusion image from at least part of the initial diffusion scan data, acquiring target diffusion scan data by means of a diffusion weighted magnetic resonance scan at a target b-value higher than each of the initial b-values, and generating the synthetic diffusion image by performing a cost function based reconstruction to apply a fidelity term in k space to the synthetic diffusion image based on at least the initial diffusional image, and the target diffusion scan data.

13 Claims, 5 Drawing Sheets

(51) Int. Cl.
 *A61B 5/00* (2006.01)
 *G01R 33/56* (2006.01)
 *G01R 33/565* (2006.01)
(52) U.S. Cl.
 CPC .......... *A61B 5/7207* (2013.01); *G01R 33/565* (2013.01); *G01R 33/5608* (2013.01)
(58) Field of Classification Search
 CPC ....... A61B 5/00; A61B 5/0037; A61B 5/7207; A61B 5/055
 See application file for complete search history.

(56) References Cited

U.S. PATENT DOCUMENTS

| | | | |
|---|---|---|---|
| 2011/0052031 | A1 | 3/2011 | Feiweier et al. |
| 2011/0280456 | A1* | 11/2011 | Sussman ............ G01R 33/5608 382/131 |
| 2013/0012805 | A1 | 1/2013 | Penn |
| 2015/0146956 | A1 | 5/2015 | Gall et al. |
| 2016/0054420 | A1 | 2/2016 | Wong |
| 2016/0084929 | A1* | 3/2016 | Dale .................. G01R 33/5608 324/309 |

OTHER PUBLICATIONS

Ogura et al "Optimal B-Values for Generation of Computed High-B Value DW Images" American Journal of Roentgenology, Apr. 2016, vol. 206, No. 4, p. 713-718.

Blackledge et al "Computed Diffusion Weighted MR Imaging May Improve Tumor Detection" Radiology vol. 261, No. 2, Nov. 2011 p. 573-581.

Shafiee et al, "Apparent Ultra-High—Value Diffusion-Weighted Image Reconstruction via Hidden Conditional Random Fields" IEEE Transactions on Medical Imaging, vol. 34, No. 5, May 2015 p. 1111-1124.

Ueno et al "Computed diffusion-weighted imaging using 3-T magnetic resonance imaging for prostate cancer diagnosis" Eur Radiol. (2013) 23; p. 3509-3516.

Glaister et al Quantitative Investigative Analysis of Tumour Separability in the Prostate Gland using Ultra-high b-value Computed Diffusion Imaging; 34th Annual International Conference of the IEEE EMBS, Aug. 28-Sep. 1, 2012.

Grant et al "Comparison of calculated and acquired high b value diffusion-weighted imaging in prostate cancer" Abdom Imaging, (2015) 40; p. 578-586.

Peled et al High b-Value Apparent Diffusion-Weighted Images From CURVE-Ball DTI; Journal of Magnetic Resonance Imaging, 30: p. 243-348 (2009).

Rosenkrantz et al "Computed Diffusion-weighted Imaging of the Prostate at 3T: Impact on Image Quality and Tumor Detection" Eur. Radiol. (2013) 23: p. 3170-3177.

Moti Friedman "Improved Multi B-Value Diffusion Weighted MRI of the Body by Simultaneous Model Estimation and Image Reconstruction" Sep. 22, 2013.

Haldar et al "Improved Diffusion Imaging Through SNR-Enhancing Joint Reconstruction" Magnetic Resonance in Med. vol. 69, No. 1, Mar. 5, 2012 p. 277-289.

Shafiee Mohammad Javad et al: "Apparent Ultra-High b-Value Diffusion-Weighted Image Reconstruction via Hidden Conditional Random Fields",IEEE Transactions on Medical Imaging, IEEE Service Center, Piscataway, NJ, US, vol. 34, No. 5, May 1, 2015.

Maas M.C. et al: "Contrast-to-noise ratio in extrapolated and measured high b-value diffusion weighted prostate MR images",Proceedings of the International Society for Magnetic Resonance in Medicine, 19th Annual Meeting and Exhibition, Montreal, Quebec, May 7-13, 2011, vol. 19, No. 3066, Apr. 23, 2011.

Haewon Nam et al: "Distortion correction of high b-valued and high angular resolution diffusion images using terative simulated images", Neuroimage, Academic Press, Orlando, FL, US,vol. 57, No. 3, May 3, 2011(May 3, 2011),pp. 968-978.

* cited by examiner

DIFFUSION MRI METHOD FOR GENERATING A SYNTHETIC DIFFUSION IMAGE AT A HIGH B-VALUE

CROSS REFERENCE TO RELATED APPLICATIONS

This application is a U.S. national phase application of International Application No. PCT/EP2016/079359, filed on Dec. 1, 2016, which claims the benefit of PCT/CN2015/096853 filed Dec. 9, 2015 and EP Application Serial No. 161669883.3 filed on Apr. 26, 2016 and are incorporated herein by reference.

TECHNICAL FIELD OF THE INVENTION

The invention relates to magnetic resonance imaging, in particular to magnetic resonance diffusion imaging.

BACKGROUND OF THE INVENTION

Magnetic resonance imaging allows anatomical and physiological features of living human and animal bodies to be observed. Recently, there has been interest in the magnetic resonance technique known as magnetic resonance diffusion imaging for the detection of cancer where the image signal is dependent upon the diffusivity of the tissue. Diffusion imaging includes diffusion weighted imaging (DWI), diffusion tensor imaging (DTI), diffusion kurtosis imaging (DKI), q-space imaging, and many other diffusion techniques. For the purpose of clarity and brevity, the description hereinafter is described with particular reference to DWI. It is to be understood that this description is for illustrative purposes and also finds application in other usage scenarios and/or diffusion imaging techniques.

DWI measures the magnitude of random motion (Brownian motion) of water molecules, which is often referred to as apparent diffusion coefficient (ADC). The physiological basis of using DWI for cancer diagnosis is that the densely packed cells within a cancer restrict the normal random motion. A low level of random motion is an indicator of cancer. DWI acquisitions are defined by their b-values, where the b-value is defined by the amplitude, duration and temporal spacing of the DWI gradients which allows for the probing of different diffusion coefficients. DWI images with different b-values and different diffusion directions are normally combined with one another in order to calculate ADC maps. Moreover, researchers have proposed many models to describe the complicated diffusion in human tissues, such as the mono-exponential model which refers to the so-called ADC map, and the bi-exponential model which refers to IVIM map, DTI map, and DKI map, which are collectively referred to as diffusion parameter map herein. The IVIM model is preferred in tissues with high perfusion, DKI model has been investigated in liver, and DTI model has been studied in brain mostly. Diffusion weighted images and/or diffusion parameter maps can be used by radiologists to distinguish areas with low random motion that are suspicious for cancer.

DWI collected at higher b-values, e.g., greater than 1000 s/mm$^2$, allows for increased delineation between tumors and normal tissues. However, a challenge faced in using high b-values is that the acquired images at high b-values have low signal-to-noise ratio (SNR) and serious distortion. An alternative approach to achieve high b-value DWI is computed DWI in which diffusion weighted images using high b-values can be mathematically derived from lower b-value DWI images using a computational model, rather than directly acquired. Although many studies have suggested the images generated by computed DWI are diagnostically comparable to acquired high b-value DWI, radiologists still have no enough confidence in feasibility of computed DWI since the computed DWI is only a simulation of acquired high b-value DWI. Moreover, the computed DWI often results in abnormal contrast, which further undermines radiologists' confidence in computed DWI. Furthermore, the image quality of computed DWI depends on computational models, b-values, tissues of interest, etc., which calls for more clinical investigation to evaluate the efficacy of computed DWI before it is widely accepted.

"Improved Multi B-Value Diffusion-Weighted MRI of the Body by Simultaneous Model Estimation and Image Reconstruction" by Freiman Moti discloses a Bayesian model of the expected signal with the signal decay model utilized as the prior information, which allows a simultaneous model estimation and image reconstruction for multiple b-values at once.

SUMMARY OF THE INVENTION

The invention provides for a magnetic resonance imaging system, a method, and a computer program product in the independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa. The contents of the memory and storage may duplicate each other or items depicted as being in one may be stored or copied in the other.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins by the antenna of a Magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer. Magnetic resonance data may also be referred to as k-space data. K-space is a formalism widely used in magnetic resonance imaging. In MRI physics, k-space is the 2D or 3D Fourier transform of the MR image measured. In practice, k-space often refers to the temporary image space, usually a matrix of complex value, in which data from digitized MR signals are stored during data acquisition.

Embodiment of the present invention provides a method for generating a synthetic diffusion image. The method comprises the steps of acquiring multiple sets of initial diffusion scan data by means of diffusion weighted magnetic resonance scans at multiple initial b-values, deriving an initial diffusion image from at least part of the initial diffusion scan data, acquiring target diffusion scan data by means of a diffusion weighted magnetic resonance scan at a target b-value higher than each of the initial b-values, and generating the synthetic diffusion image by performing a cost function based reconstruction to apply a fidelity term in k space to the synthetic diffusion image based on at least the initial diffusional image and the target diffusion scan data. The synthetic diffusion image is at least one of a synthetic diffusion DWI image at the target b-value and a synthetic diffusion parameter map. An initial diffusion parameter map is derived from the at least part of the initial diffusion scan data to provide the initial diffusion image when the synthetic diffusion image is the synthetic diffusion parameter map, and an initial computed DWI image at the target b-value is derived from the at least part of the initial diffusion scan data to provide the initial diffusion image when the synthetic diffusion image is the synthetic diffusion DWI image at the target b-value.

Owing to usage of both the actually acquired target diffusion scan data at higher b-values and the initial diffusion image computed from lower b-values, the synthetic diffusion image generated for higher b-values can achieve an improved SNR and distortion compared with the diffusion image reconstructed directly from acquired diffusion scan data at higher b-values. In addition, due to usage of the diffusion scan data actually acquired at higher b-values, radiologists' confidence in the synthetic diffusion image is increased as compared to the computed diffusion image which solely relies on a mathematical computation of diffusion scan data acquired at lower b-values. Moreover, the synthetic diffusion image generated according to the present invention can result in a normal contrast, which further increases radiologist's confidence in feasibility of the synthetic diffusion image.

According to one embodiment of the present invention, the step of deriving the initial diffusion image further comprises the steps of reconstructing at least two initial diffusion weighted images (DWI images) based upon the initial diffusion scan data associated with at least two different initial b-values, calculating an apparent diffusion coefficient (ADC) map based upon the at least two initial DWI images, and calculating an initial computed DWI image at the target b-value as the initial diffusion image based on the calculated ADC map. Advantageously, the initial computed DWI image at the target b-value can be used as prior information about the cost function based reconstruction.

According to another embodiment of the present invention, the step of generating the synthetic diffusion image further comprises generating a synthetic DWI image at the target b-value as the synthetic diffusion image by minimizing the cost function composed of a weighted sum of at least a fidelity term measuring similarities between the diffusion scan data acquired at the target b-value and k space data of the synthetic DWI image and a constraint term measuring similarities between the synthetic DWI image and the initial computed DWI image. Advantageously, by using the initial computed DWI image as prior information, the synthetic diffusion image reconstructed by minimizing associated cost function achieves an improved SNR and distortion compared with the DWI image reconstructed directly from acquired diffusion scan data at higher b-values. Meanwhile, radiologists' confidence in feasibility of the synthetic diffusion image is higher than the computed DWI image which see-solely relies on a mathematical computation of diffusion scan data acquired at lower b-values.

According to yet another embodiment of the present invention, the step of deriving the initial diffusion image further comprises reconstructing at least two initial DWI images based upon the initial diffusion scan data associated with at least two different initial b-values, and calculating an initial diffusion parameter map as the initial diffusion image based upon the at least two initial DWI images. Advantageously, the specific property of diffusion parameter map, e.g., piecewise smoothness, can be used as prior information about the cost function based measurement map reconstruction, thereby eliminating the necessities of full DWI image reconstruction prior to measuring diffusion parameter map from the reconstructed DWI image.

According to yet another embodiment of the present invention, the step of generating the synthetic diffusion image further comprises generating a synthetic diffusion parameter map as the synthetic diffusion image by minimizing the cost function composed of a sum of fidelity terms measuring similarities between the initial diffusion scan data acquired at each initial b-value and target b-value and k space data of a DWI image calculated for each corresponding initial b-value and target b-value based upon the synthetic diffusion parameter map. Advantageously, as compared to the diffusion parameter map calculated from two DWI images, a more accurate and reliable synthetic diffusion parameter map can be generated by means of the cost function based reconstruction. Moreover, a higher quality DWI image can be computed using the more accurate synthetic diffusion parameter map.

According to yet another embodiment of the present invention, the synthetic diffusion parameter map is one of an ADC map, a diffusion coefficient and kurtosis (DKI) map, and an intravoxel incoherent motion (IVIM) map. Advantageously, the cost function based diffusion map reconstruction is applicable to various diffusion map measurements.

According to yet another embodiment of the present invention, the method further comprises the step of applying a spatial regularization term to the cost function based reconstruction to improve a signal to noise (SNR) ratio of the synthetic diffusion image.

Embodiment of the present invention further provides a magnetic resonance imaging system (100) for generating a synthetic diffusion image. The magnetic resonance imaging system comprises a data receiver (20) configured to receive multiple sets of initial diffusion scan data acquired by means of diffusion weighted magnetic resonance scans at multiple initial b-values and target diffusion scan data acquired by means of a diffusion weighted magnetic resonance scan at a target b-value higher than each of the initial b-values, an initial diffusion image generator (22) configured to derive an initial diffusion image from at least part of the initial diffusion scan data, and a synthetic diffusion image generator (24) configured to generate the synthetic diffusion image by performing a cost function based reconstruction to apply a fidelity term in k space to the synthetic diffusion image based on at least the initial diffusional image, and the target diffusion scan data. The synthetic diffusion image is at least one of a synthetic diffusion DWI image at the target b-value and a synthetic diffusion parameter map. An initial diffusion parameter map is derived from the at least part of the initial diffusion scan data to provide the initial diffusion image when the synthetic diffusion image is the synthetic diffusion parameter map, and an initial computed DWI image at the target b-value is derived from the at least part of the initial diffusion scan data to provide the initial diffusion image when the synthetic diffusion image is the synthetic diffusion DWI image at the target b-value.

According to one embodiment of the present invention, the initial diffusion image generator (22) further comprises a DWI image generator (206) configured to reconstruct at least two initial DWI images based upon the initial diffusion scan data associated with at least two different initial b-values, an ADC map calculator (208) configured to calculate the ADC map based upon the at least two initial DWI images, and a DWI image calculator (210) configured to calculate an initial computed DWI image at the target b-value based on the calculated ADC map and output the initial computed DWI image as the initial diffusion image to the synthetic diffusion image generator.

According to another embodiment of the present invention, the synthetic diffusion image is a synthetic DWI image, and the synthetic diffusion image generator is further configured to minimize the cost function composed of a weighted sum of at least a fidelity term measuring similarities between the diffusion scan data acquired at the target b-value and k space data of the synthetic DWI image and a constraint term measuring similarities between the synthetic DWI image and the initial computed DWI image.

According to yet another embodiment of the present invention, the initial diffusion image generator (22) further comprises a DWI image generator (406) configured to reconstruct at least two initial DWI images based upon the initial diffusion scan data associated with at least two different initial b-values, an initial diffusion parameter map calculator (408) configured to calculate an initial diffusion parameter map based upon the at least two initial DWI images and output the initial diffusion parameter map as the initial diffusion image to the synthetic diffusion image generator.

According to yet another embodiment of the present invention, the synthetic diffusion image is a synthetic diffusion parameter map selected from one of an ADC map, a diffusion coefficient and kurtosis (DKI) map, and an intravoxel incoherent motion (IVIM) map, and the synthetic diffusion image generator is further configured to minimize the cost function composed a sum of fidelity terms measuring similarities between the initial diffusion scan data acquired at each initial b-value and target b-value and k space data of a DWI image calculated for each corresponding initial b-value and target b-value based upon the synthetic diffusion parameter map.

Embodiment of the present invention further provides a computer program product comprising machine executable instructions for execution by a processor (28) controlling a magnetic resonance imaging system (100). Execution of the machine executable instructions cause the processor (28) to acquire multiple sets of initial diffusion scan data by means of diffusion weighted magnetic resonance scans at multiple initial b-values, derive an initial diffusion image from at least part of the initial diffusion scan data, acquire target diffusion scan data by means of a diffusion weighted magnetic resonance scan at a target b-value higher than each of the initial b-values, and generate the synthetic diffusion image by performing a cost function based reconstruction to apply a fidelity term in k space to the synthetic diffusion image based on at least the initial diffusional image, and the target diffusion scan data. The synthetic diffusion image is at least one of a synthetic diffusion DWI image at the target b-value and a synthetic diffusion parameter map. An initial diffusion parameter map is derived from the at least part of the initial diffusion scan data to provide the initial diffusion image when the synthetic diffusion image is the synthetic diffusion parameter map, and an initial computed DWI image at the target b-value is derived from the at least part of the initial diffusion scan data to provide the initial diffusion image when the synthetic diffusion image is the synthetic diffusion DWI image at the target b-value.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
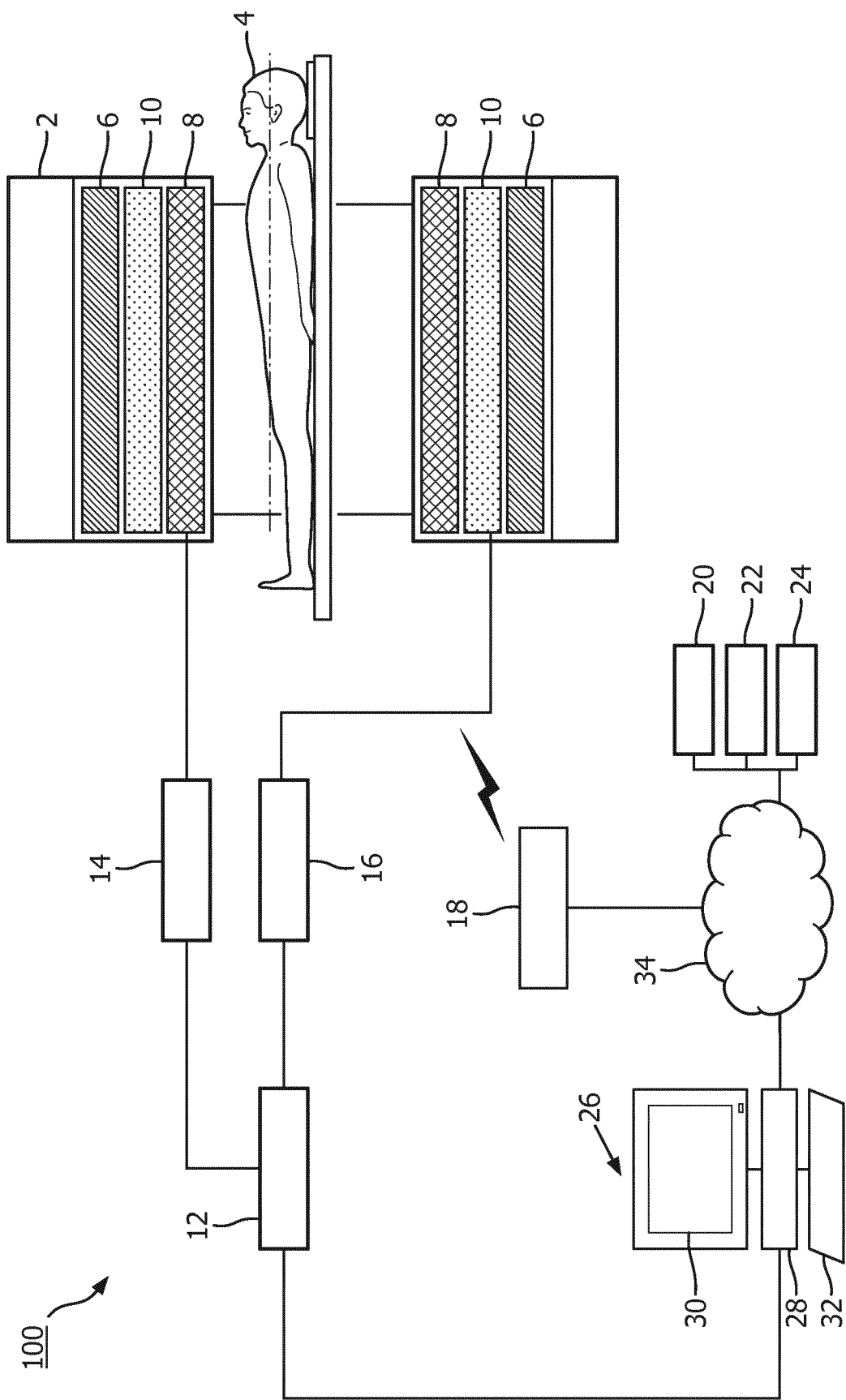
FIG. 1 schematically illustrates a magnetic resonance imaging system for generating a synthetic diffsion image according to one embodiment of the present invention.

With reference to FIG. 1, an embodiment of a magnetic resonance (MR) system 100 is schematically illustrated. The MR system 100 includes a MR scanner 2 such as an open system or c-type scanner, a horizontal bore scanner, and the like shown in a cross section view. The MR scanner 2 includes an opening or bore that defines an examination region in which a subject 4 is placed for a spectroscopic and/or imaging examination. The MR scanner 2 includes one or more main magnets 6 with a C-shape ferrous flux return path in an open system, one or more radio frequency (RF) coils 8, and one or more gradient coils 10. A C-type main magnet 6 generates a vertical static $B_0$ field such as vertical static field. Alternatively, a bore magnet generates a horizontal static $B_0$ field.

The MR system 100 includes a sequence controller 12 which controls the operation of a DWI sequence, a RF transmitter unit 14 controlling the operation of the RF coils 8, and a gradient controller 16 controlling the operation of the gradient coils 10. The communication between the controlling units and the corresponding coils can be wireless or wired. The RF coils 8 generate radio frequency pulses which excite and manipulate resonance in tissue of the subject 4. The RF coils 8 can include a whole body coil and/or a local coil such as a torso coil, hand coil, shoulder coil, knee coil, etc.

The one or more gradient coils 10 generate gradient magnetic fields across the static magnetic field and region of interest of the subject 4 to spatially encode the induced resonance, induced gradient echoes, and the like. The gradient fields are applied across the region of interest in different directions and/or using different b-values such that data redundancy occurs from overlap in the received image data at any single voxel. The b-value represents the integral of the diffusion encoding gradient duration and strength, and is measured in sec/mm$^2$ units. The sequence controller 12 configures the RF coils and the gradient coils to excite and manipulate resonance in tissues of the subject based on a DWI sequence.

The MR system 100 includes a RF receiver unit 18, which receives diffusion weighted magnetic resonance (MR-DWI) signals. As the resonance decays in the tissue of the subject, weak radio frequency signals or MR-DWI signals are received by a radio frequency antenna such as the RF coils 8 and/or local coils, and sent to the RF receiver unit 18. The RF receiver unit 18 transforms the MR-DWI signals into diffusion scan data in k-space.

The MR system 100 includes a data receiver 20, an initial diffusion image generator 22 and a synthetic diffusion image generator 24. The data receiver 20 receives diffusion scan data from the RF receiver unit 18. The diffusion scan data includes initial diffusion scan data acquired by means of fully or partially sampled diffusion weighted magnetic resonance scans at initial b-values, and target diffusion scan data acquired by means of fully or partially sampled diffusion weighted magnetic resonance scans at one or more target b-values. The target b-value is higher than each initial b-value. The initial diffusion image generator 22 derives an initial diffusion image from at least part of the initial diffusion scan data. In one embodiment, the initial diffusion image is an initial DWI image computed for the target b-value. Alternatively, the initial diffusion image is an initial diffusion parameter map resulting from DWI measurement, e.g., an ADC map, a diffusion coefficient and kurtosis (DKI) map, or an intravoxel incoherent motion (IVIM) map. No matter what type of initial diffusion image is derived, the amount of initial diffusion scan data is large enough for the deriving, especially for the initial diffusion scan data by means of partially sampled diffusion weighted magnetic resonance scans at initial b-values. The synthetic diffusion image generator 24 generates the synthetic diffusion image by performing a cost function based reconstruction to apply a fidelity constraint to the synthetic diffusion image based on the initial diffusion scan data, the initial diffusion image, and the target diffusion scan data. Advantageously, owing to using the initial diffusion image computed from lower b-values as prior information, the synthetic diffusion image generated for higher b-values can achieve an improved SNR and distortion compared with the diffusion image reconstructed directly from acquired diffusion scan data at higher b-values. In addition, due to usage of the diffusion scan data at higher b-values, radiologists' confidence in the synthetic diffusion image is increased as compared to the computed diffusion image which solely relies on a mathematical computation of diffusion scan data acquired at lower b-values. Moreover, the synthetic diffusion image generated according to the present invention can result in a normal contrast, which further increases radiologists' confidence in feasibility of the synthetic diffusion image.

The MR system 100 further includes a workstation 26, which includes an electronic processor or electronic processing device 28, a display device 30 which displays the reconstructed synthetic diffusion images, menus, panels, and user controls, and at least one input device 32 which inputs a healthcare practitioner selections and/or commands. For example, the healthcare practitioner can select the DWI sequence from a menu displayed on the display device. The workstation 26 can be a desktop computer, a laptop, a tablet, a mobile computing device, a smartphone, and the like. The display device 30 can include a computer monitor, a touch screen, Cathode ray tube (CRT), Storage tube, Flat panel display, Light-emitting diode (LED) displays, Electroluminescent display (ELD), Plasma display panels (PDP), Liquid crystal display (LCD), Organic light-emitting diode displays (OLED), a projector, and the like. The input device 32 can be a keyboard, a mouse, a microphone, and the like.

The various units or modules 20, 22, and 24 are suitably embodied by an electronic data processing device, such as the electronic processor or electronic processing device 28 of the workstation 26, or by a network-based server computer operatively connected with the workstation 26 by a network 34, or so forth. The user interface is suitably embodied by the workstation 26. Moreover, the disclosed data receiving, initial diffusion image generation, and synthetic diffusion image reconstruction techniques are suitably implemented using a non-transitory storage medium storing instructions (e.g., software) readable by an electronic data processing device and executable by the electronic data processing device to perform the disclosed techniques.

Figure 2:
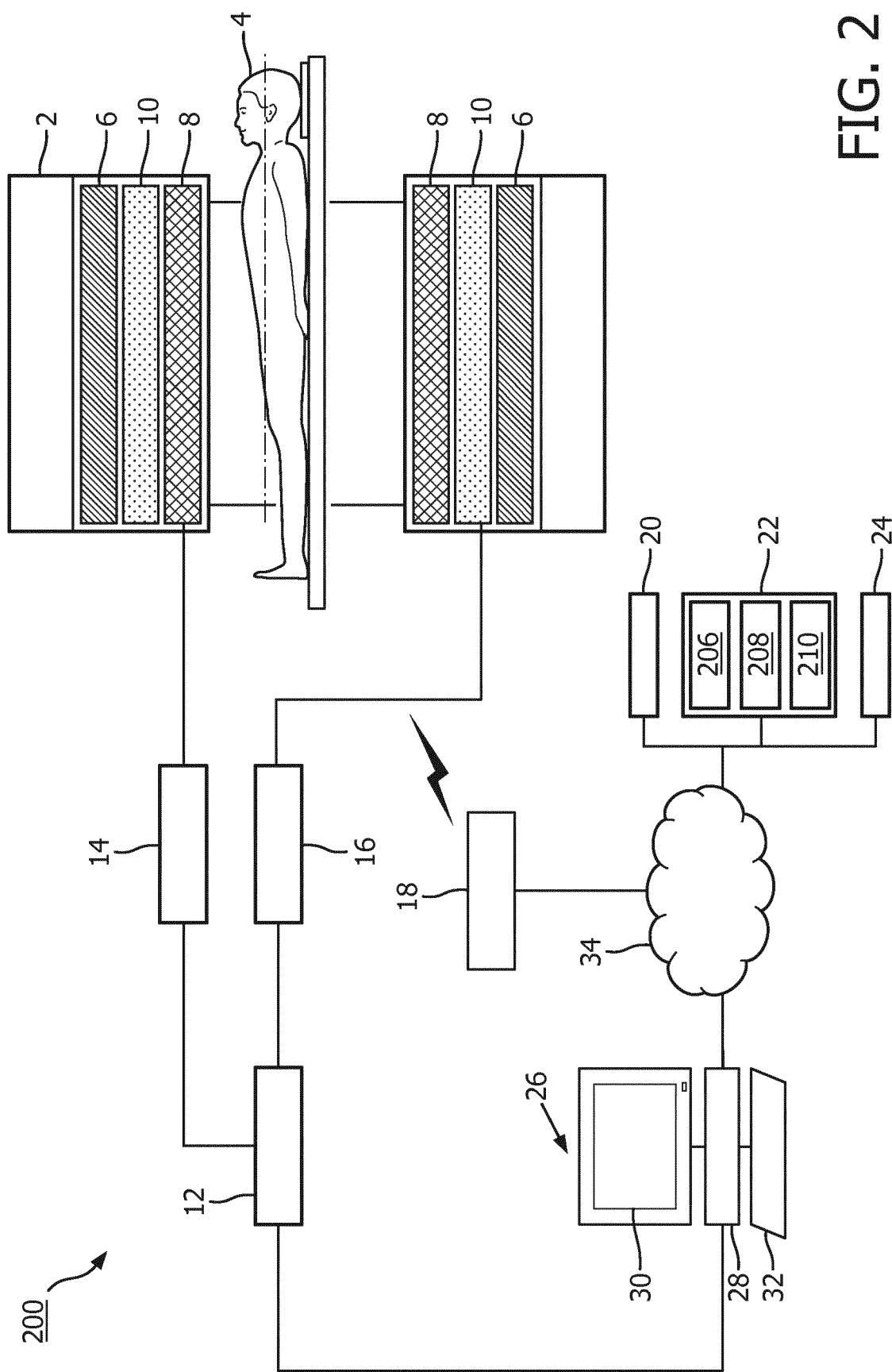
FIG. 2 schematically illustrates a magnetic resonance imaging system for generating a synthetic DWI image according to one embodiment of the present invention.

With reference to FIG. 2, a magnetic resonance imaging system 200 configured to generate a synthetic DWI image is illustrated. Since the diffusion image refers to DWI image in the embodiment of FIG. 2, the initial and synthetic diffusion image generators are herein also referred to as initial and synthetic DWI generators, respectively. The initial DWI image generator 22 further includes a low b-value DWI image generator 206, an ADC map calculator 208 and a high b-value DWI image calculator 210. According to diffusion signal decay model, DWI images associated with two or more b-values from the low b-value DWI image generator 206 allows the ADC of tissues to be calculated by the ADC map calculator 208 on a voxel-by-voxel in conformity with the following equation $$S_{l1} = S_{l2} \cdot \exp(-(b_{l1} - b_{l2}) \cdot ADC) \quad (1),$$

where ADC represents to-be-calculated ADC value, $b_{l1}$ represents the b-value associated with signal intensity $S_{l1}$, and $S_{l2}$ represents the signal intensity associated with the b-value $b_{l2}$. For example, imaging is performed with b-values of 0 and 900 sec/mm$^2$, ADC map is calculated by using diffusion scan data from both b-values and referred to as ADC*. Once the ADC value is known, the high b-value DWI image calculator 210 uses it to extrapolate the expected signal intensity $S_h$ for each image voxel to the higher target b-value $b_h$ according to the following equation, $$S_h = S_0^* \cdot \exp(-b_h \cdot ADC^*) \quad (2),$$

where ADC* and $S_0^*$ are pixel-wise estimations of ADC and signal intensity $S_0$ associated with b-value of 0 sec/mm$^2$, respectively, thus generating the initial computed DWI image $S_h$. For example, an initial computed DWI image $S_h$ at b-value of 1500 sec/mm$^2$ can be computed according to the equation (2).

It should be understood by the skilled in the art that the diffusion signal decay model for calculating the initial computed DWI image is not limited to ADC, other diffusion signal decay model is also contemplated, e.g., a diffusion coefficient and kuitosis model, an intravoxel incoherent motion model or the like.

Upon completion of generating the initial computed DWI image, synthetic DWI image generator 24 subjects estimation of signal intensity $SS_h$ associated with higher target b-value $b_h$ of the synthetic diffusion image to a set of reconstruction constraints and minimization of the associated cost function. One form of the cost function for synthetic diffusion image reconstruction is given as $$SS_h = \mathrm{argmin}_{SS_h}(\|m - F(SS_h)\|_2^2 + \alpha \|SS_h - S_h\|_2^2 \quad (3),$$

where $SS_h$ represents to-be-reconstructed synthetic DWI image associated with the higher target b-value $b_h$ whose initial value can be the initial computed DWI image $S_h$, m represents diffusion scan data actually acquired at higher target b-value $b_h$, which can be fully or partially sampled, F represents one or more encoding operators, e.g., Fourier transform, mask sampling, coil sensitivity map, etc., $\| \|2$ represents the L2-norm, which produces the least squares solution and can be substituted by any other type of measure of deviation between images, $\alpha$ represents a weighting factor controlling the relative contributions of the fidelity term $\|m - F(SS_h)\|_2^2$ and the constraint term $\|SS_h - S_h\|_2^2$. The fidelity term $\|m - F(SS_h)\|_2^2$ forces the solution $SS_h$ to adhere to the acquired diffusion scan data m. The constraint term $\|SS_h - S_h\|_2^2$ forces the solution $SS_h$ to adhere to the initial computed DWI image $S_h$. Put it another way, a weighted sum of the fidelity term and constraint term forces the generated synthetic diffusion image to achieve a minimized sum of a fidelity term measuring a first similarities between k space data of the synthetic diffusion image and the acquired diffusion scan data m and a constraint term measuring a second similarities between the synthetic diffusion image and the initial computed DWI image.

Alternatively, a spatial regularization term can further be applied to the cost function based reconstruction to improve a signal to noise ratio (SNR) of the synthetic DWI image. In this case, the cost function is given by $$SS_h = \mathrm{argmin}_{SS_h}(\|m - F(SS_h)\|_2^2 + \alpha \|SS_h - S_h\|_2^2 + \beta \cdot G(SS_h)) \quad (4),$$

where G (■) represents the regularization function, such as L1 norm of wavelet transformation $\|\Psi(SS_h)\|_1$, total variation $TV(SS_h)$, etc., and $\beta$ represents a weighting factor controlling the relative contributions of the spatial regularization term.

Figure 3:
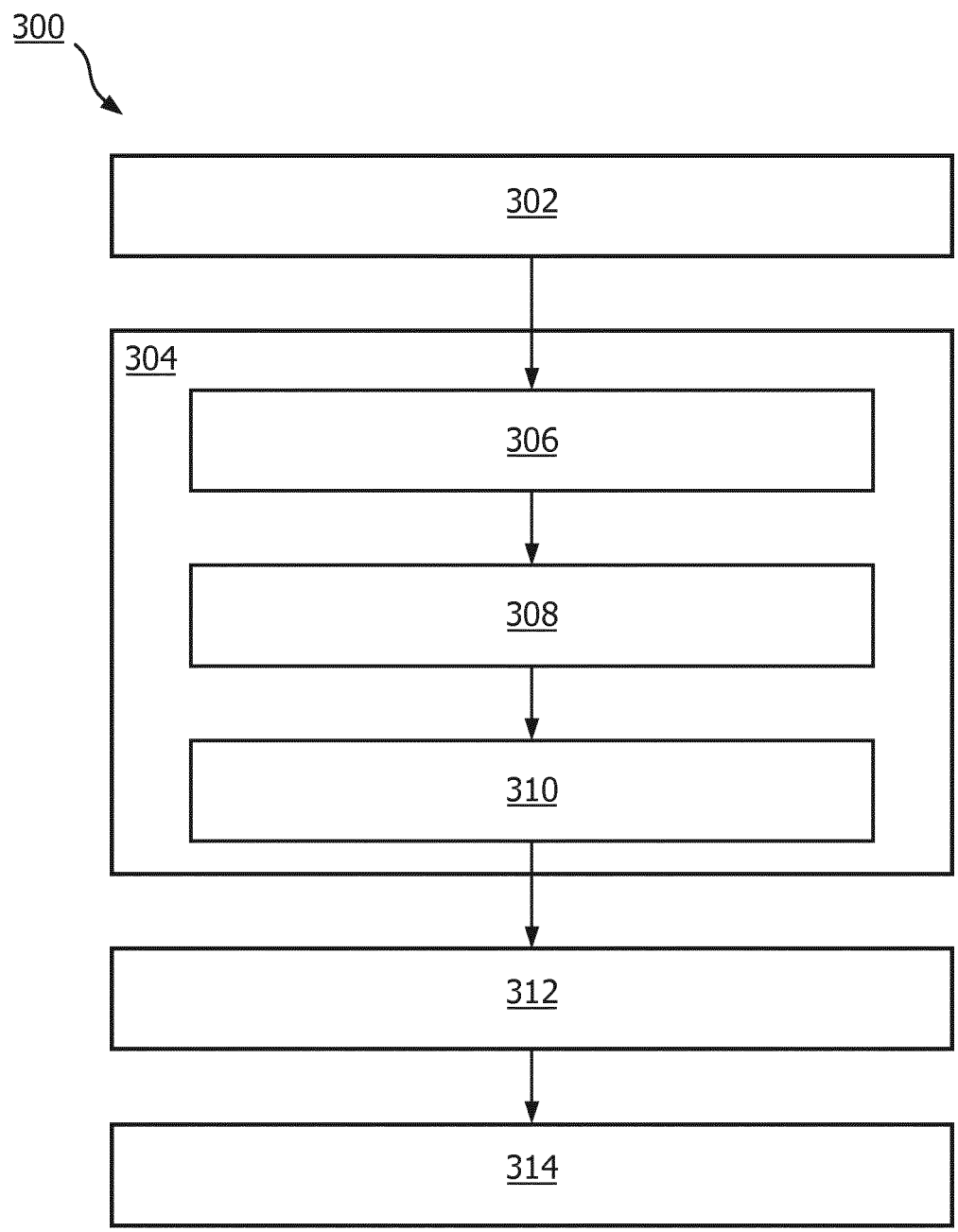
FIG. 3 illustrates a flow chart of a method for generating a synthetic DWI image according to one embodiment of the present invention.

FIG. 3 illustrates a flow chart 300 of a method for generating a synthetic diffusion image by the magnetic resonance imaging system 200 according to one embodiment of the present invention. FIG. 3 is described in combination with FIG. 2.

At a step 302, initial diffusion scan data is acquired by means of diffusion weighted magnetic resonance scans at a lot of initial b-values. In one embodiment, the magnetic resonance scanner 2 performs the MR-DWI acquisition at multiple initial b-values to provide initial diffusion scan data at the RF receiver 18. Preferably, the initial b-values are different from each other and relatively low, e.g., below 1000 sec/mm$^2$. These initial diffusion scan data is acquired by the data receiver 20 for further processing.

At a step 304, an initial diffusion image is derived from at least part of the initial diffusion scan data. In one embodiment, the step 304 further comprises a step 306 of reconstructing at least two initial DWI images based upon the initial diffusion scan data associated with at least two different initial b-values, a step 308 of calculating an ADC map based upon the at least two initial DWI images, and a step 310 of calculating an initial computed DWI image at the target b-value as the initial diffusion image based on the calculated ADC map. Referring back to FIG. 2, the low b-value DWI image generator 206 generates at least two lower b-value DWI images, e.g., $S_{l1}$ and $S_{l2}$ associated with b-values of 900 sec/mm$^2$ and 0 sec/mm$^2$, respectively. The ADC map calculator 208 calculates the estimated ADC* based on the at least two lower b-value DWI images in conformity with equation (1). By using more than two lower b-value DWI images, an averaged more accurate ADC estimation ADC* can be determined. With the known ADC*, the high b-value DWI image generator 210 generates the initial computed DWI image by using the known ADC* to extrapolate the expected signal intensity $S_h$ for each image voxel to the higher target b-value $b_h$, e.g., 1500 sec/mm$^2$.

At a step 312, target diffusion scan data is acquired by means of a diffusion weighted magnetic resonance scan at a target b-value higher than each of the initial b-values. In one embodiment, the magnetic resonance scanner 2 performs the MR-DWI acquisition at the target b-value to provide target diffusion scan data at the RF receiver 18. The target b-value is higher than each of initial b-value and preferable above 1000 sec/mm$^2$, e.g., the target b-value of 1500 sec/mm$^2$. The target diffusion scan data is acquired by the data receiver 20 for further processing.

At a step 314, the synthetic diffusion image is generated by performing a cost function based reconstruction to apply a fidelity constraint to the synthetic diffusion image based on the initial diffusion scan data, the initial diffusional image, and the target diffusion scan data. In one embodiment, the synthetic DWI image generator 24 generates the synthetic DWI image at the target b-value by subjecting the estimation of signal intensity $SS_h$ associated with the higher target b-value $b_h$ to the cost function given by the equation (3) or (4).

Figure 4:
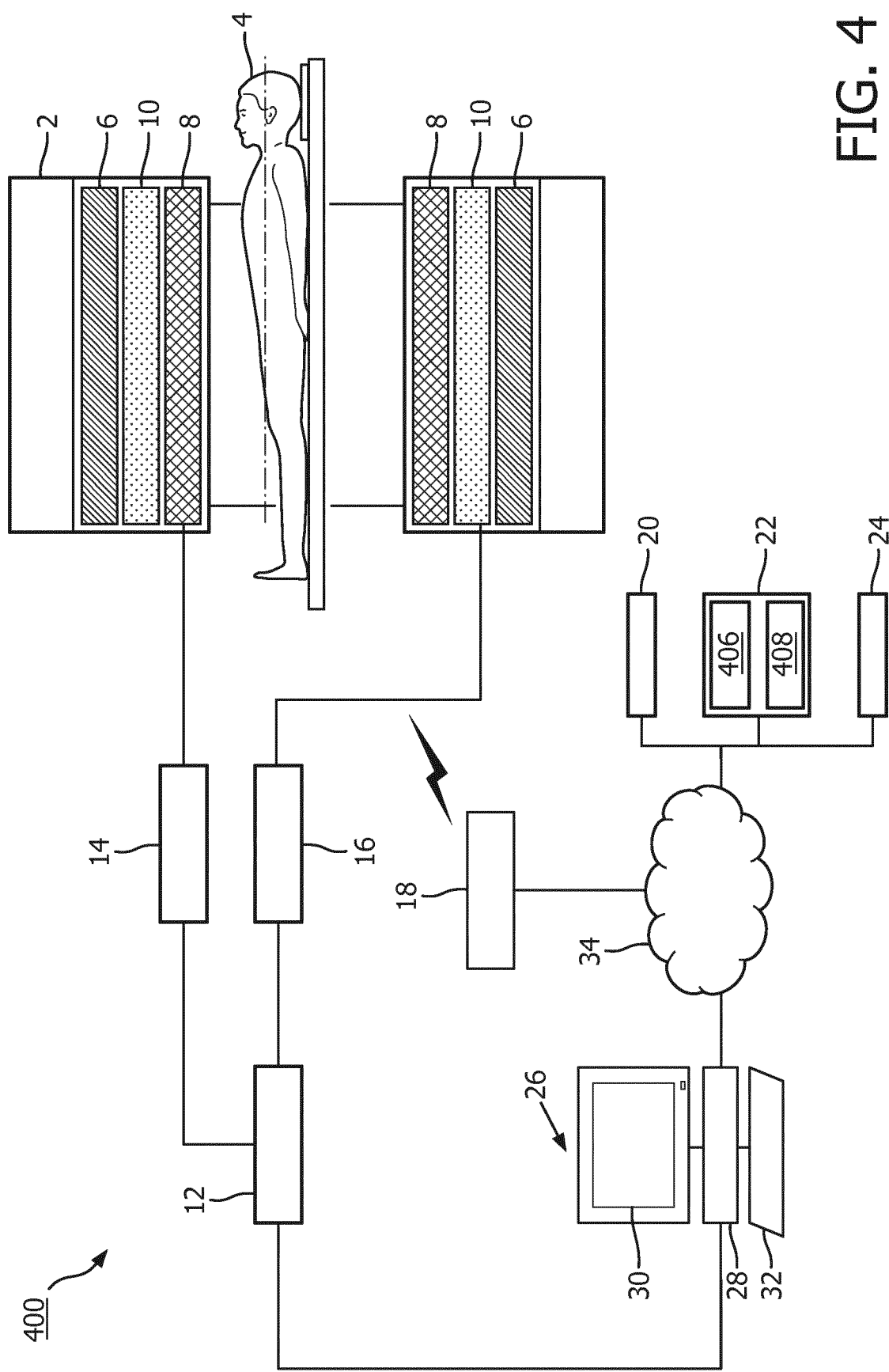
FIG. 4 schematically illustrates a magnetic resonance imaging system for generating a synthetic diffusion parameter map according to one embodiment of the present invention.

With reference to FIG. 4, a magnetic resonance imaging system 400 configured to generate a synthetic diffusion parameter map is illustrated. Since the diffusion image refers to diffusion parameter map in the embodiment of FIG. 4, the initial and synthetic diffusion image generators are herein also referred to as initial and synthetic parameter map generators, respectively. The initial diffusion parameter map generator 22 further includes a low b-value DWI image generator 406 and an initial diffusion parameter map calculator 408. As aforementioned, DWI measurements includes various parameter measurements, including but not limited to, ADC map, DKI map, and IVIM map. The embodiment of FIG. 4 is described with particular reference to ADC map. Similar to the low b-value DWI image generator 206, the low b-value DWI image generator 406 generates low b-value DWI images. Similar to the ADC map calculator 208, the initial diffusion parameter map calculator 408 calculates the estimated ADC map ADC* based upon the low b-value DWI images. Different from the synthetic DWI image generator 24 which estimates the synthetic DWI image using an ADC map derived from the initial DWI image computed from lower b-value diffusion scan data, the synthetic diffusion parameter map generator 24 reconstructs the synthetic ADC map using a k-space based fidelity term about the cost function given by $$ADC = \operatorname{argmin}_{ADC}(\Sigma_{b_i} \| m_{b_i} - F(S_0^* \cdot \exp(-b_i \cdot ADC) \|_2^2) \quad (5),$$

where ADC represents to-be-reconstructed ADC map whose initial value can be ADC*, which is estimated based upon the acquired low b-value diffusion scan data, $b_i$ represents each high/low b-value used for MR-DWI scan, $m_{b_i}$ represents the acquired diffusion scan data associated with the high/low b-value $b_i$, $S_0^*$ is pixel-wise estimation of signal intensity $S_0$ associated with b value of 0 sec/mm². $\Sigma$ represents a sum of fidelity terms, each of which measures similarities between the acquired diffusion scan data $m_{b_i}$ associated with the b-value $b_i$ and k-space data of the DWI image associated with the b-value $b_i$ and computed based upon the to-be-reconstructed ADC map. Advantageously, the synthetic ADC map computed according to the equation (5) is more accurate than ADC* computed from the equation (1), thereby further improving the quality of computed DWI image when the synthetic ADC map is used in place of ADC* for DWI image computation. Similarly, the cost function according to equation (5) can also include a spatial regularization term to generate a piecewise-constant ADC map.

As aforementioned, the parameter measurements also include, but not limited to, DKI map and IVIM map. For DKI map measurement, the synthetic diffusion parameter map generator 24 reconstructs the synthetic DKI map according to the following equation $$(D,K) = \operatorname{argmin}_{D,K}(\Sigma_{b_i} \| m_{b_i} - F(S_0^* \cdot \exp(-b_i D + b_i^2 D^2 \cdot K/6)) \|_2^2) \quad (6),$$

where D represents to-be-reconstructed diffusion coefficient map (D map) and K represents to-be-reconstructed kurtosis map (K map). For IVIM map measurement, the synthetic diffusion parameter map generator 24 reconstructs the synthetic IVIM map according to the following equation (7)

$$(D,D^*,f) = \operatorname{argmin}_{D,D^*,f}(\Sigma_{b_i} \| m_{b_i} - F\{S_0^* \cdot [(1-f)\exp(-b_i \cdot D) + f \exp(-b_i \cdot D^*)]\} \|_2^2),$$

where D, D* and f represent to-be reconstructed pure diffusion coefficient map, perfusion-related diffusion coefficient and perfusion fraction map, respectively. For the purpose of brevity, the equation of other parameter measurements will not be herein descried in details. However, it should be understood by the skilled in the art that the present invention is readily applicable to reconstructing various kinds of parameter map to improve its accuracy.

Figure 5:
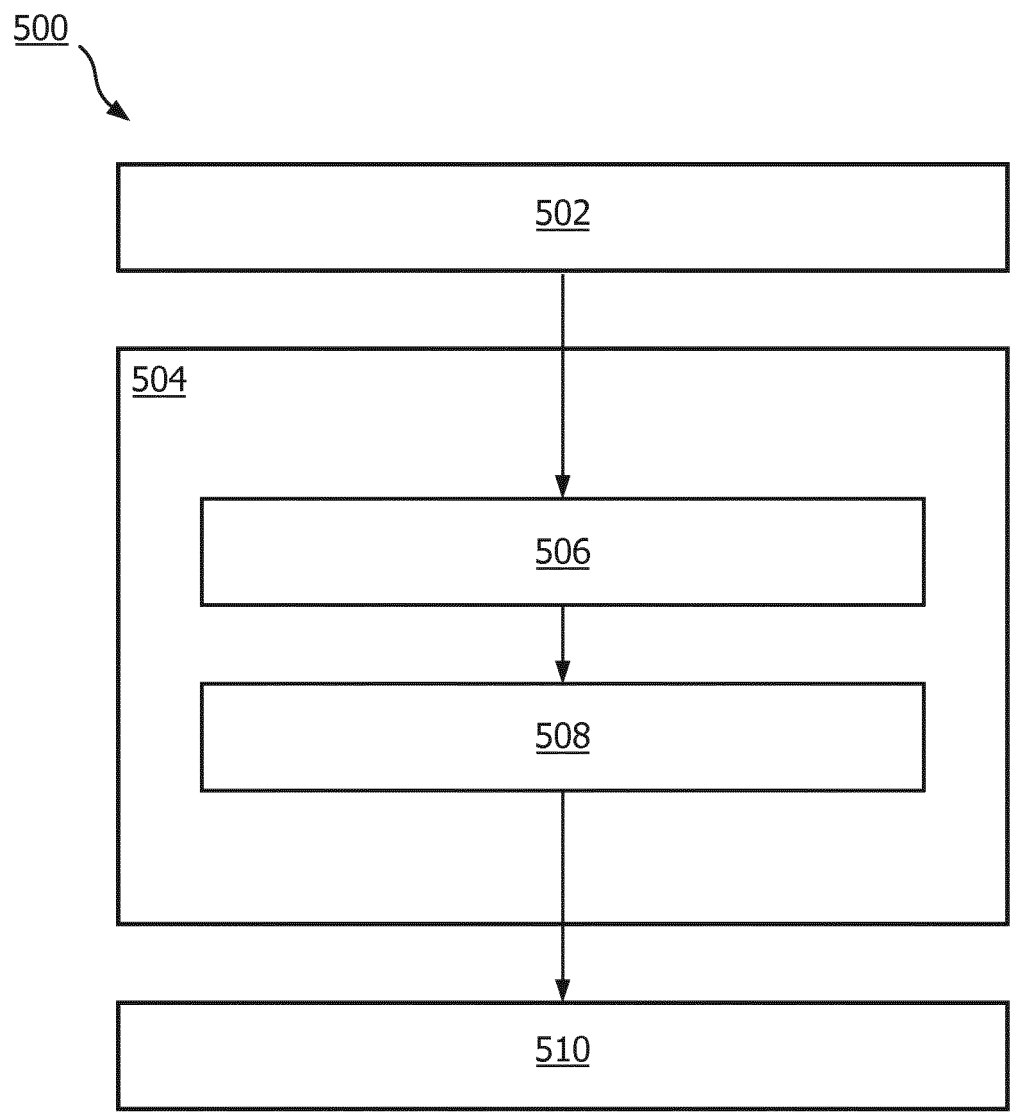
FIG. 5 illustrates a flow chart of a method for generating a synthetic diffusion parameter map according to one embodiment of the present invention.

FIG. 5 illustrates a flow chart 500 of a method for generating a synthetic diffusion image by the magnetic resonance imaging system 400 according to one embodiment of the present invention. FIG. 5 is described in combination with FIG. 4.

At a step 502, initial diffusion scan data and target diffusion scan data is acquired by means of diffusion weighted magnetic resonance scans at lower initial b-values and one or more higher target b-values, respectively. In one embodiment, the magnetic resonance scanner 2 performs the MR-DWI acquisition at multiple lower initial b-values, e.g., b-values of 900 sec/mm² and 0 sec/mm², to provide initial diffusion scan data, and the MR-DWI acquisition at one or more higher target b-values, e.g., b-value of 1500 sec/mm², to provide target diffusion scan data at the RF receiver 18. Preferably, each of the initial b-values are different from each other and relatively low, e.g., below 1000 sec/mm², and each of the target b-values are different from each other and relatively high, e.g., above 1000 sec/mm². These initial and target diffusion scan data is acquired by the data receiver 20 for further processing.

At a step 504, an initial diffusion image is derived from at least part of the initial diffusion scan data. In one embodiment, the step 504 further comprises a step 506 of reconstructing at least two initial DWI images based upon the initial diffusion scan data associated with at least two different initial b-values, and a step 508 of calculating an initial diffusion parameter map based on the at least two initial DWI images. Referring back to FIG. 4, the low b-value DWI image generator 406 generates at least two lower b-value DWI images, e.g., $S_{I1}$ and $S_{I2}$ associated with b-values of 900 sec/mm² and 0 sec/mm², respectively. The initial diffusion parameter map calculator 408 calculates the estimated ADC* based on the at least two lower b-value DWI images in conformity with equation (1).

At a step 510, the synthetic diffusion image is generated by performing a cost function based reconstruction to apply a fidelity constraint to the synthetic diffusion image based on the initial diffusion scan data, the initial diffusional image, and the target diffusion scan data. In one embodiment, the synthetic diffusion parameter map generator 24 generates the synthetic diffusion parameter map at the target b-value by subjecting the estimation of parameter map to the cost function given by any of the equations (5)-(7).

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for generating a synthetic diffusion image, the method comprising:

acquiring a plurality of initial diffusion scan data by means of diffusion weighted magnetic resonance scans at a plurality of initial b-values;

deriving an initial diffusion image from at least part of the initial diffusion scan data;

acquiring target diffusion scan data by means of a diffusion weighted magnetic resonance scan at a target b-value higher than each of the initial b-values; and generating the synthetic diffusion image by performing a cost function based reconstruction using at least the initial diffusion image and the target diffusion scan data to apply a fidelity term in k space to the synthetic diffusion image, wherein the synthetic diffusion image is at least one of a synthetic diffusion weighted imaging (DWI) image at the target b-value and a synthetic diffusion parameter map, and wherein an initial diffusion parameter map is derived from the at least part of the initial diffusion scan data to provide the initial diffusion image when the synthetic diffusion image is the synthetic diffusion parameter map, and an initial computed DWI image at the target b-value is derived from the at least part of the initial diffusion scan data to provide the initial diffusion image when the synthetic diffusion image is the synthetic diffusion DWI image at the target b-value.

2. The method of claim 1, wherein the step of deriving the initial diffusion parameter map further comprises:

reconstructing at least two initial DWI images based upon the initial diffusion scan data associated with at least two different initial b-values;

calculating the initial diffusion parameter map based upon the at least two initial DWI images.

3. The method of claim 1, wherein the step of generating the synthetic diffusion parameter map further comprises:

minimizing the cost function composed of a sum of fidelity terms measuring similarities between the initial diffusion and target scan data acquired at each initial b-value and target b-value and k space data of a DWI image calculated for each corresponding initial b-value and target b-value based upon the synthetic diffusion parameter map.

4. The method of claim 1, wherein the synthetic diffusion parameter map is one of an ADC map, a diffusion coefficient and kurtosis (DKI) map, and an intravoxel incoherent motion (IVIM) map.

5. The method of claim 1, wherein the step of deriving the initial computed DWI image at the target b-value further comprises:

reconstructing at least two initial diffusion weighted images (DWI images) based upon the initial diffusion scan data associated with at least two different initial b-values;

calculating an apparent diffusion coefficient (ADC) map based upon the at least two initial DWI images; and calculating the initial computed DWI image at the target b-value based on the calculated ADC map.

6. The method of claim 1, wherein the step of generating the synthetic diffusion DWI image at the target b-value further comprises:

minimizing the cost function composed of a weighted sum of at least the fidelity term measuring similarities between the diffusion scan data acquired at the target b-value and k space data of the synthetic diffusion DWI image and a constraint term measuring similarities between the synthetic diffusion DWI image and the initial computed DWI image at the target b-value.

7. The method of claim 1, further comprising:

applying a spatial regularization term to the cost function based reconstruction to improve a signal to noise (SNR) ratio of the synthetic diffusion image.

8. A magnetic resonance imaging system for generating a synthetic diffusion image comprising:

a data receiver configured to receive initial diffusion scan data acquired by means of diffusion weighted magnetic resonance scans at a plurality of initial b-values and target diffusion scan data acquired by means of a diffusion weighted magnetic resonance scan at a target b-value higher than each of the initial b-values;

an initial diffusion image generator configured to derive an initial diffusion image from at least part of the initial diffusion scan data; and a synthetic diffusion image generator configured to generate the synthetic diffusion image by performing a cost function based reconstruction using at least the initial diffusion image and the target diffusion scan data to apply a fidelity term in k space to the synthetic diffusion image, wherein the synthetic diffusion image is at least one of a synthetic diffusion weighted imaging (DWI) image at the target b-value and a synthetic diffusion parameter map, and wherein an initial diffusion parameter map is derived from the at least part of the initial diffusion scan data to provide the initial diffusion image when the synthetic diffusion image is the synthetic diffusion parameter map, and an initial computed DWI image at the target b-value is derived from the at least part of the initial diffusion scan data to provide the initial diffusion image when the synthetic diffusion image is the synthetic diffusion DWI image at the target b-value.

9. The magnetic resonance imaging system of claim 8, wherein the initial diffusion image generator further comprises:

a DWI image generator configured to reconstruct at least two initial DWI images based upon the initial diffusion scan data associated with at least two different initial b-values;

an initial diffusion parameter map calculator configured to calculate the initial diffusion parameter map based upon the at least two initial DWI images and output the initial diffusion parameter map to the synthetic diffusion image generator.

10. The magnetic resonance imaging system of claim 8, wherein the synthetic diffusion parameter map is selected from one of an ADC map, a diffusion coefficient and kurtosis (DKI) map, and an intravoxel incoherent motion (IVIM) map, and wherein the synthetic diffusion image generator is further configured to minimize the cost function composed of a sum of fidelity terms measuring similarities between the initial and target diffusion scan data acquired at each initial b-value and target b-value and k space data of a DWI image calculated for each corresponding initial b-value and target b-value based upon the synthetic diffusion parameter map.

11. The magnetic resonance imaging system of claim 8, wherein the initial diffusion image generator further comprises:

a DWI image generator configured to reconstruct at least two initial DWI images based upon the initial diffusion scan data associated with at least two different initial b-values;

an ADC map calculator configured to calculate the ADC map based upon the at least two initial DWI images; and a DWI image calculator configured to calculate the initial computed DWI image at the target b-value based on the calculated ADC map and output the initial computed DWI image at the target b-value to the synthetic diffusion image generator.

12. The magnetic resonance imaging system of claim 8, wherein the synthetic diffusion image generator is further configured to minimize the cost function composed of a weighted sum of at least the fidelity term measuring similarities between the diffusion scan data acquired at the target b-value and k space data of the synthetic DWI image and a constraint term measuring similarities between the synthetic DWI image and the initial computed DWI image at the target b-value.

13. A computer program product comprising machine executable instructions for execution by a processor controlling a magnetic resonance imaging system, wherein execution of the machine executable instructions cause the processor to:

acquire a plurality of initial diffusion scan data by means of diffusion weighted magnetic resonance scans at a plurality of initial b-values;

derive an initial diffusion image from at least part of the initial diffusion scan data;

acquire target diffusion scan data by means of a diffusion weighted magnetic resonance scan at a target b-value higher than each of the initial b-values; and generate the synthetic diffusion image by performing a cost function based reconstruction using at least the initial diffusion image and the target diffusion scan data to apply a fidelity term in k space to the synthetic diffusion image, wherein the synthetic diffusion image is at least one of a synthetic diffusion weighted imaging (DWI) image at the target b-value and a synthetic diffusion parameter map, and wherein an initial diffusion parameter map is derived from the at least part of the initial diffusion scan data to provide the initial diffusion image when the synthetic diffusion image is the synthetic diffusion parameter map, and an initial computed DWI image at the target b-value is derived from the at least part of the initial diffusion scan data to provide the initial diffusion image when the synthetic diffusion image is the synthetic diffusion DWI image at the target b-value.

* * * * *